United States Patent
Köhler et al.

(10) Patent No.: US 6,232,423 B1
(45) Date of Patent: May 15, 2001

(54) PROCESS FOR PREPARING MIXTURES OF LINEAR ORGANOPOLYSILOXANES

(75) Inventors: Thomas Köhler, Kastl; Manfred Meisenberger, Burghausen, both of (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/413,123

(22) Filed: Oct. 6, 1999

(30) Foreign Application Priority Data

Oct. 8, 1998 (DE) .............................................. 198 46 397

(51) Int. Cl.⁷ .................................................. C08G 77/08
(52) U.S. Cl. .............................................. 528/12; 556/450
(58) Field of Search ................................. 556/450; 528/12

(56) References Cited

U.S. PATENT DOCUMENTS

| | | | |
|---|---|---|---|
| 2,758,124 | * 8/1956 | Schwenker | 260/448.2 |
| 2,832,794 | 4/1958 | Gordon . | |
| 3,646,093 | 2/1972 | Puthet . | |
| 4,855,472 | * 8/1989 | Burkhardt | 556/459 |
| 5,476,916 | 12/1995 | Pachaly et al. . | |

FOREIGN PATENT DOCUMENTS

| | | |
|---|---|---|
| 954 198 | 12/1956 | (DE) . |
| 1 937 739 | 1/1970 | (DE) . |
| 0 485 977 A2 | 5/1992 | (EP) . |
| 0 515 082 A1 | 11/1992 | (EP) . |

OTHER PUBLICATIONS

XP 000274401, Journal of General Chemistry USSR, vol. 61, No. 6, pp. 1257–1261.
XP 002120279, Polymer Science USSR, vol. 28, No. 7, pp. 1630–1638.

* cited by examiner

*Primary Examiner*—Margaret G. Moore
(74) *Attorney, Agent, or Firm*—Brooks & Kushman P.C.

(57) ABSTRACT

Mixtures of linear organopolysiloxanes of the general formula 1 for $$R_3SiO\text{—}(SiR_2O)_n\text{—}SiR_3 \qquad (1)$$

are produced by a process in which organochlorosilanes of the general formula 2

$$R_{4-y}SiCl_y \qquad (2)$$

where
R is identical or different and is a hydrogen atom or an unsubstituted or substituted hydrocarbon radical having from 1 to 18 carbon atoms,
Y is 1 or 2, and
n is 0 or an integer from 1 to 50,
are reacted continuously in a closed circulation system with water which may, if desired, have been acidified with hydrochloric acid, where the HCl concentration in the hydrochloric acid discharged is less than 25% by weight. Low molecular weight oligomer mixtures substantially free of both cyclic organosiloxanes and organosilicon compounds containing Si—Cl are economically produced.

16 Claims, No Drawings

PROCESS FOR PREPARING MIXTURES OF LINEAR ORGANOPOLYSILOXANES

TECHNICAL FIELD

The invention relates to a process for preparing mixtures of linear organopolysiloxanes.

BACKGROUND ART

The preparation of organopolysiloxanes by hydrolysis and condensation of halosilanes is known. Organopolysiloxanes are also frequently prepared starting from mixtures of low-molecular-weight and high-molecular-weight organopolysiloxanes, which are equilibrated to give low-molecular-weight mixtures by adding a suitable catalyst. However, the latter method is not an adequate solution for preparing organopolysiloxanes with a very low degree of condensation. The known preparation processes are also particularly directed at forming cyclic organopolysiloxanes with a ring size of from 3 to 6 siloxane units.

No processes are known for directly preparing mixtures of linear low-molecular-weight siloxanes with a low proportion of hexamethyldisiloxane and of cyclic siloxanes, but the targeted products can be prepared by mixing the individual components in a very time-consuming and costly manner.

A continuous process for hydrolyzing organochlorosilanes is described in DE-C 954 198. This reaction is carried out in a loop reactor. The concentration of the discharged hydrochloric acid produced during the reaction is at least 25%. This high concentration leads to a crude hydrolysate with unhydrolyzed and undesirable Si—Cl units.

DISCLOSURE OF INVENTION

The object on which the invention is based is to provide a process which allows the cost-effective production of linear, low-molecular-weight organopolysiloxanes with a defined makeup and a reduced proportion of hexamethyldisiloxane, in which very little cyclic low-molecular-weight organopoly-siloxanes and organopolysiloxanes containing Si—Cl units are produced.

BEST MODE FOR CARRYING OUT THE INVENTION

The invention provides a process for preparing mixtures of linear organopolysiloxanes of the general formula 1

$$R_3SiO-(SiR_2O)_n-SiR_3 \quad (1)$$

in which organochlorosilanes of the general formula 2

$$R_{4-y}SiCl_y \quad (2)$$

where
R is identical or different and is a hydrogen atom or an unsubstituted or substituted hydrocarbon radical having from 1 to 18 carbon atoms,
y is 1 or 2, and
n is 0 or an integer from 1 to 50,
are reacted continuously in a closed circulation system with water which may, if desired, have been acidified with hydrochloric acid, where the HCl concentration in the hydrochloric acid discharged is less than 25% by weight.

Using the present process, the proportions of cyclic, low-molecular-weight organopolysiloxanes achieved in the product are not more than 1% by weight, in particular not more than 0.5% by weight.

The radical R is preferably a hydrocarbon radical having from 1 to 18 carbon atoms and unsubstituted or substituted with fluorine, chlorine or cyano radicals and preferably free from ethylenically or acetylenically unsaturated bonds.

Examples of hydrocarbon radicals R are alkyl radicals such as the methyl, ethyl, n-propyl, isopropyl, n-butyl, isobutyl, tert-butyl, n-pentyl, isopentyl, neopentyl and tert-pentyl radicals, hexyl radicals such as the n-hexyl radical; heptyl radicals such as the n-heptyl radical; octyl radical s such a s the n-octyl radical, and isooctyl radicals, such as the 2,2,4-trimethylpentyl radical; nonyl radicals such as the n-nonyl radical, decyl radicals such as the n-decyl radical; dodecyl radicals such as the n-dodecyl radical; octadecyl radicals such as the n-octadecyl radical; cycloalkyl radicals such as cyclopentyl, cyclohexyl and cycloheptyl radicals and methylcyclohexyl radicals; aryl radicals, such as the phenyl, naphthyl and anthryl and phenanthryl radicals; alkaryl radicals, such as o-, m- and p-tolyl radicals, xylyl radicals and ethylphenyl radicals; aralkyl radicals, such as the benzyl radical and the alpha- and the β-phenylethyl radicals.

Examples of substituted hydrocarbon radicals R are cyanoalkyl radicals, such as the β-cyanoethyl radical, and halogenated hydrocarbon radicals, for example haloalkyl radicals, such as the 3,3,3-trifluoro-n-propyl radical, the 2,2,2,2',2',2'-hexafluoroisopropyl radical and the heptafluoroisopropyl radical, and haloaryl radicals, such as the o-, m- and p-chlorophenyl radicals.

R is preferably a linear alkyl radical, in particular having from 1 to 10 carbon atoms, particularly from 1 to 6 carbon atoms. Particularly preferred radicals R are ethyl and, in particular, methyl radicals.

n is preferably not more than 20, in particular not more than 10.

The mixtures preferably have the following makeup:

n=0: the proportion is from 0 to 99 percent, preferably from 0 to 80 percent, and in particular from 0 to 60 percent.

n=1: the proportion is from 0 to 99 percent, preferably from 10 to 70 percent, and in particular from 20 to 65 percent.

n=2: the proportion is from 0 to 99 percent, preferably from 5 to 50 percent, and in particular from 10 to 35 percent.

n=3: the proportion is from 0 to 99 percent, preferably from 0 to 20 percent, and in particular from 2 to 15 percent.

n=4: the proportion is from 0 to 99 percent, preferably from 0 to 10 percent, and in particular from 0 to 5 percent.

n=5: the proportion is from 0 to 99 percent, preferably from 0 to 5 percent, and in particular from 0 to 3 percent.

n=6: the proportion is from 0 to 99 percent, preferably from 0 to 5 percent, and in particular from 0 to 2 percent.

n=7: the proportion is from 0 to 99 percent, preferably from 0 to 5 percent, and in particular from 0 to 1 percent.

n=8: the proportion is from 0 to 99 percent, preferably from 0 to 5 percent, and in particular from 0 to 1 percent.

n=9: the proportion is from 0 to 99 percent, preferably from 0 to 5 percent, and in particular from 0 to 0.5 percent.

n=10: the proportion is from 0 to 99 percent, preferably from 0 to 5 percent, and in particular from 0 to 0.5 percent.

Preferred organochlorosilanes of the general formula 2 are vinylmethyldichlorosilane, phenylmethyldichlorosilane, divinyldichlorosilane, diphenyldichlorosilane, methyldichlorosilane, vinyldimethylchlorosilane, dimethyldichlorosilane and trimethylchlorosilane. Particularly preferred organochlorosilanes of the general formula 2 are dimethyldichlorosilane and trimethylchlorosilane.

The organochlorosilanes of the general formula 2 are preferably used in stoichiometrically molar amounts in the process. Preference is given here to proportional amounts of $R_3SiX:R_2SiX_2$ of from 1:100 to 100:1, in particular from 1:20 to 1:1. It is, however, also possible to use amounts of organochlorosilanes which differ from this.

The process is preferably carried out at temperatures of from 20 to 150° C., in particular from 30 to 100° C. The pressure used is preferably that of the surrounding atmosphere, i.e. 1020 hPa (abs.) or about 1020 hPa (abs.). However, higher or lower pressures may also be used if desired, preferably from 100 to 10,000 hPa (abs.), in particular up to 6000 hPa (abs.).

In the reaction, hydrolysis with water and condensation of the organochlorosilanes of the general formula 2 take place simultaneously. In the closed circulation system the reaction mixture is preferably circulated by a pump. Fresh water and the organochlorosilanes are fed continuously. Likewise, an appropriate portion of the reaction mixture composed of organopolysiloxanes of the general formula 1 and acid-enriched water are continuously discharged from the process and separated.

The concentration of HCl in the hydrochloric acid discharged is preferably from 18 to 24% by weight, in particular from 20 to 23% by weight. The HCl formed during the hydrolysis of the organochlorosilanes is converted to an aqueous hydrochloric acid by metering in water, and the concentration of the hydrochloric acid in the reaction vessel is preferably thus held constant.

If desired, a portion of the low-molecular-weight, linear organopolysiloxanes, in particular those in which n=0, is separated off, by batchwise or continuous distillation, from the organopolysiloxanes of the general formula 1 discharged, so that a defined mixture of low-molecular-weight, linear organosilicon compounds is produced. In particular, this method prepares mixtures which are not obtainable by direct continuous hydrolysis and condensation.

The distillate obtained from the distillation may, if desired, be fed back into the circulation system in the form of a mixture with the organochlorosilanes of the general formula 2. The distillate is preferably catalytically redissociated, in particular on a carbon column. The resultant cleavage product is then preferably fed back into the circulation system, if desired in the form of a mixture with the organochlorosilanes of the general formula 2.

In the examples described below all data on parts and percentages are based on weight, unless otherwise stated. Unless otherwise stated, the examples below were carried out at ambient atmospheric pressure, i.e. about 1000 hPa.

EXAMPLES

System for Preparing the Crude Hydrolysates

The loop system used is composed of a centrifugal pump with a conveying rate of 500 l per hour, a condenser with a cooling surface of 0.12 m² and of a T piece for discharging crude product and aqueous hydrochloric acid. The components are connected to one another by pipelines of a nominal width of 40 mm: the pressure side of the pump to the T piece and its lower end to the suction side of the pump. 7 l of 21% strength hydrochloric acid are pumped into this circulating system. 1.8 kg of silane mixture and 2.5 kg of water per hour are fed continuously to the circulating system via two feed lines entering between T piece and pump.

The residence time between the silane feed point and T piece is about 50 seconds. After a short period of operation the circulating liquid reaches a constant temperature of 50° C. and its HCl concentration remains at 21%.

From the upper part of the T piece the liquid is passed into the middle of a principal separator in which complete separation into aqueous and organic phase takes place. The organic phase produced generally has a residual acid content of about 200 ppm. If desired, the resultant crude organic hydrolysate can be washed with water to a residual acid content of <5 ppm.

The makeup of the crude hydrolysate can be controlled by varying the molar mixing ratio of trimethylchlorosilane (M3) and dimethyldichlorosilane (M2). The weight ratios of low-molecular-weight, linear organosilicon compounds in the crude hydrolysate as a function of the makeup of the silane mixture used here are seen in the following Table 1. The entries in the table are in weight percent as measured by gas chromatography.

TABLE 1

| Oligomer Silicon Atom Content[1] | M3/M2 Ratio | | | |
|---|---|---|---|---|
| | 2/1 | 4/1 | 6/1 | 8/1 |
| 2 | 36.00 | 54.00 | 61.00 | 69.00 |
| 3 | 24.00 | 26.00 | 25.00 | 24.00 |
| 4 | 17.00 | 13.00 | 10.00 | 5.00 |
| 5 | 9.00 | 4.00 | 2.50 | 1.00 |
| 6 | 5.00 | 1.00 | 0.70 | 0.10 |
| 7 | 3.00 | 0.50 | 0.40 | — |
| 8 | 1.00 | 1.10 | — | — |
| D4[2] | 1.00 | .20 | 0.10 | — |

[1]Numerals represent silicon atoms in linear siloxanes.
[2]Cyclotetrasiloxane content.

After the continuous hydrolysis and condensation, the crude hydrolysate produced as described above is, if desired, freed from a portion of the low-molecular-weight volatile siloxanes formed by batchwise or continuous distillation. The distillation equipment and the distillation parameters here may be selected to give in principle any desired product makeup.

The distillation of the crude hydrolysate described in column 4/1 in the list in the table above is given here as an example. The distillation frees the crude product obtained from most of the hexamethyldisiloxane formed during the hydrolysis/condensation.

System for Distillation of the Crude Hydrolysates

The distillation apparatus used is composed of a 2 l three-necked glass flask provided with a thermometer and heated by a heating mantle.

To the flask is connected a silvered glass column of length 40 cm, packed with 6 mm Raschig rings. On top of this column is a reflux condenser with distillate discharge. This allows the return ratio to be set to increase separation performance of the column and allows discharge of distillate.

1.5 l of the crude hydrolysate prepared as described above are charged to the distillation flask. Hexamethyldisiloxane is then separated off by distillation. The content of hexamethyldisiloxane in the residue here can be controlled via the maximum temperature set for the stirred material in the distillation.

In principle, increasing the temperature of the stirred material gives a lower content of hexamethyldisiloxane in the residue. As in Table 1, all amounts are in weight percent as determined by gas chromatography. Compositions obtained from distillations at various reflux ratios are presented in Table II.

TABLE 2

Siloxane Oligomer Distribution (Distilled)

| Siloxane Oligomer Distribution (Original) | | Dist. 1 | Dist. 2 | Dist. 3 | Dist. 4 | Dist. 5 | Dist. 6 | Dist. 7 |
|---|---|---|---|---|---|---|---|---|
| Si 2 | 54.00 | 49.00 | 44.00 | 35.00 | 30.00 | 20.00 | 9.00 | 6.00 |
| Si 3 | 26.00 | 28.00 | 31.00 | 30.00 | 36.00 | 42.00 | 51.00 | 52.00 |
| Si 4 | 13.00 | 14.00 | 17.00 | 21.00 | 22.00 | 24.00 | 26.00 | 27.00 |
| Si 5 | 4.00 | 5.00 | 5.00 | 9.00 | 8.00 | 9.00 | 9.00 | 9.00 |
| Si 6 | 1.00 | 1.40 | 1.50 | 3.00 | 2.30 | 3.00 | 3.00 | 4.00 |
| Si 7 | 0.50 | 0.50 | 0.70 | 1.00 | 0.80 | 1.00 | 1.00 | 1.00 |
| Si 8 | 0.10 | 0.20 | 0.20 | 0.30 | 0.30 | 0.50 | 0.50 | 0.50 |
| D 4 | 0.20 | 0.30 | 0.50 | 0.50 | 0.40 | 0.50 | 0.50 | 0.50 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing mixtures of linear organopolysiloxanes of the general formula 1

$$R_3SiO\text{—}(SiR_2O)_n\text{—}SiR_3 \quad (1)$$

in which organochlorosilanes of the general formula 2

$$R_{4-y}SiCl_y \quad (2)$$

where

R is identical or different and is a hydrogen atom or an unsubstituted or substituted hydrocarbon radical having from 1 to 18 carbon atoms, y is 1 or 2, and n is 0 or an integer from 1 to 50, are reacted continuously in a closed circulation system with water which may, if desired, have been acidified with hydrochloric acid, where the HCl concentration in the hydrochloric acid discharged is from 18% to 24% by weight, said mixtures of linear organopolysiloxanes containing not more than 1% cyclic low molecular weight organopolysiloxanes.

2. The process of claim 1, wherein the radical R is a hydrocarbon radical having from 1 to 18 carbon atoms and is unsubstituted or substituted with fluorine, chlorine or cyano radicals, and is free from ethylenically and acetylenically unsaturated bonds.

3. The process of claim 1, wherein the organochlorosilanes used are selected from the group consisting of vinylmethyldichlorosilane, phenylmethyldichlorosilane, divinyldichlorosilane, diphenyldichlorosilane, methyldichlorosilane, vinyldimethylchlorosilane, dimethyldichlorosilane and trimethylchlorosilane.

4. The process of claim 2, wherein the organochlorosilanes used are selected from the group consisting of phenylmethyldichlorosilane, diphenyldichlorosilane, methyldichlorosilane, dimethyldichlorosilane and trimethylchlorosilane.

5. The process of claim 1, in which the concentration of HCl in the hydrochloric acid discharged is from 20 to 23% by weight.

6. The process of claim 2, in which the concentration of HCl in the hydrochloric acid discharged is from 20 to 23% by weight.

7. The process of claim 3, in which the concentration of HCl in the hydrochloric acid discharged is from 20 to 23% by weight.

8. The process of claim 4, in which the concentration of HCl in the hydrochloric acid discharged is from 20 to 23% by weight.

9. The process of claim 1 wherein a portion of low-molecular-weight, linear organopolysiloxane product is removed by distillation from the discharged organopolysiloxanes of the general formula 1.

10. The process of claim 2 wherein a portion of low-molecular-weight, linear organopolysiloxane product is removed by distillation from the discharged organopolysiloxanes of the general formula 1.

11. The process of claim 5 wherein a portion of low-molecular-weight, linear organopolysiloxane product is removed by distillation from the discharged organopolysiloxanes of the general formula 1.

12. The process as claimed in claim 9, in which a distillate obtained from the distillation is fed back into the circulation system in the form of a mixture with organochlorosilanes of the general formula 2.

13. The process as claimed in claim 9, in which the distillate obtained is catalytically redissociated and the resultant cleavage product is fed back into the circulation system.

14. The process of claim 1 wherein the amount of cyclotetrasiloxanes in said mixtures of linear organopolysiloxanes is not more than 1% by weight.

15. The process of claim 1 wherein the amount of low molecular weight cyclic organopolysiloxanes in said mixtures of linear organopolysiloxanes is not more than 0.5% by weight.

16. The process of claim 1 wherein the amount of cyclotetrasiloxanes in said mixtures of linear organopolysiloxanes is not more than 0.5% by weight.

* * * * *